(12) United States Patent
Cancellieri et al.

(10) Patent No.: US 11,883,362 B2
(45) Date of Patent: Jan. 30, 2024

(54) ASSEMBLY FIXTURE DEVICE FOR ATTACHMENT OF VIAL ADAPTER TO DRUG VIAL

(71) Applicant: Becton Dickinson and Company Limited, Dun Laoghaire (IE)

(72) Inventors: Jude Cancellieri, Oakland, NJ (US); Kivilcim Eralp, New York, NY (US); Paul Paia Marici, Piscataway, NJ (US); Derek Hugger, Goffstown, NH (US); James J. Kennedy, III, Mont Vernon, MA (US); Daniel Hamilton, Mont Vernon, MA (US)

(73) Assignee: Becton Dickinson and Company Limited, Dun Laoghaire (IE)

( * ) Notice: Subject to any disclaimer, the term of this patent is extended or adjusted under 35 U.S.C. 154(b) by 1018 days.

(21) Appl. No.: 16/374,034

(22) Filed: Apr. 3, 2019

(65) Prior Publication Data
US 2019/0307644 A1 Oct. 10, 2019

Related U.S. Application Data

(60) Provisional application No. 62/652,964, filed on Apr. 5, 2018.

(51) Int. Cl.
*B67B 7/92* (2006.01)
*B67B 3/22* (2006.01)
(Continued)

(52) U.S. Cl.
CPC ........... *A61J 1/2006* (2015.05); *A61J 1/2003* (2015.05); *A61J 1/2048* (2015.05); *B65B 3/003* (2013.01);
(Continued)

(58) Field of Classification Search
CPC .... B67B 3/00; B67B 3/22; B67B 1/06; B67B 7/16; B67B 1/04; B67B 1/00; B67B 6/00; B67C 3/242; B67C 2007/0066; F16B 2/12
(Continued)

(56) References Cited

U.S. PATENT DOCUMENTS 924,360 A * 6/1909 Kirkegaard ............... B67C 7/00
53/271
4,489,766 A 12/1984 Montada
(Continued)

FOREIGN PATENT DOCUMENTS

CN 201880724 U 6/2011
CN 106315483 A 1/2017
(Continued)

*Primary Examiner* — Tom Rodgers
(74) *Attorney, Agent, or Firm* — The Webb Law Firm

(57) ABSTRACT

An assembly fixture device for attaching a vial adapter to a vial includes a base, a support member secured to the base, a handle connected to the support member, a vial adapter grip assembly connected to the handle and comprising an adapter grip member configured to engage and hold a vial adapter, and a vial grip assembly connected to the base comprising first and second grip members that are movable relative to each other and configured to engage and hold a vial. The first grip member is biased toward the second grip member to provide a vial engagement force, where the vial engagement force is about constant when a distance between the first and second grip members is less than 40 mm.

18 Claims, 16 Drawing Sheets

(51) Int. Cl.
    *A61J 1/20*     (2006.01)
    *B65B 3/00*     (2006.01)
    *B65B 7/16*     (2006.01)
    *B65B 51/14*     (2006.01)
    *B65B 3/04*     (2006.01)
    *B65B 43/54*     (2006.01)
    *A61J 1/10*     (2006.01)
    *A61M 5/178*     (2006.01)

(52) U.S. Cl.
    CPC ............... *B65B 3/04* (2013.01); *B65B 7/161* (2013.01); *B65B 43/54* (2013.01); *B65B 51/142* (2013.01); *B67B 3/22* (2013.01); *B67B 7/92* (2013.01); *A61J 1/10* (2013.01); *A61J 1/2089* (2013.01); *A61J 1/2096* (2013.01); *A61M 5/1782* (2013.01)

(58) Field of Classification Search
    USPC ...... 81/3.31, 3.32, 3.09; 29/428, 426.1, 248; 211/85.3
    See application file for complete search history.

(56) References Cited

U.S. PATENT DOCUMENTS

| | | |
|---|---|---|
| 4,623,344 A | 11/1986 | Eriksson |
| 5,468,233 A | 11/1995 | Schraga |
| 6,006,798 A | 12/1999 | Lindquist |
| 9,168,202 B2 | 10/2015 | Clouser et al. |
| 2012/0184938 A1 | 7/2012 | Lev et al. |
| 2014/0026388 A1* | 1/2014 | Warrick ............... F16B 2/12 29/428 |

FOREIGN PATENT DOCUMENTS

| | | |
|---|---|---|
| JP | 360949 U | 6/1991 |
| JP | 2006131285 A | 5/2006 |
| JP | 2016527975 A | 9/2016 |
| JP | 2017532107 A | 11/2017 |
| WO | 2011039747 A1 | 4/2011 |
| WO | 2015017858 A1 | 2/2015 |
| WO | 2016041948 A1 | 3/2016 |
| WO | 2017066406 A1 | 4/2017 |

* cited by examiner

ASSEMBLY FIXTURE DEVICE FOR ATTACHMENT OF VIAL ADAPTER TO DRUG VIAL

CROSS-REFERENCE TO RELATED APPLICATION

The present application claims priority to U.S. Provisional Application Ser. No. 62/652,964, entitled "Assembly Fixture Device for Attachment of Vial Adaptor to Drug Vial", filed Apr. 5, 2018, the entire disclosure of which is hereby incorporated by reference.

BACKGROUND OF THE INVENTION

Field of the Invention

The present invention relates to an assembly fixture device for attaching a vial adaptor to a drug vial.

Description of Related Art

Medical drugs and solvents are often supplied in glass or plastic containers, such as vials, bottles, or bags, which are sealed by a rubber, plastic or elastomeric bung, stopper, membrane, or puncturable cap. Such sealing members prevent deterioration or contamination of the drug, allow the contents of a container to be mixed by shaking, and prevent the contents of the container from leaking out and contaminating the surroundings. A cannula or a hollow spike comprising a flow channel and an opening that communicates with the flow channel is usually inserted through such a sealing member to supply fluids to the container and to withdraw fluid therefrom.

Vial adapters are commonly used for accessing the containers and utilize a piercing member that penetrates the sealing member of a container and defines an opening at a distal end of the piercing member. Typically, after the piercing member accesses the vial, the vial is inverted to withdraw the medicament from the container. Many conventional vial adapters will be locked to the container or vial after the piercing member fully enters the vial. Due to the force required to connect the vial adapter onto the drug vial or container, assembly fixtures are typically used to assist in connecting the vial adapter to the drug vial.

SUMMARY OF THE INVENTION

In one embodiment, an assembly fixture device for attaching a vial adapter to a vial includes a base having a first side and a second side positioned opposite the first side, a support member secured to the base, with the support member having a first end and a second end positioned opposite the first end, a handle connected to the support member, the handle being movable between a first position and a second position, a vial adapter grip assembly connected to the handle, with the vial adapter grip assembly comprising an adapter grip member configured to engage and hold a vial adapter and the vial adapter grip assembly having a first position when the handle is in the first position and a second position when the handle is in the second position, and a vial grip assembly connected to the base. The vial grip assembly includes first and second grip members that are movable relative to each other and configured to engage and hold a vial, with the first grip member biased toward the second grip member to provide a vial engagement force. The vial engagement force is about constant when a distance between the first and second grip members is less than 40 mm. The vial gripper assembly is intended to center the vial, regardless of the size of the vial, so that the spike pierces the center of the vial stopper.

The vial engagement force may be both about constant when a distance between the first and second grip members is less than 40 mm and from 2.50-2.75 N when the distance between the first and second grip members is less than 40 mm.

The vial engagement force may be both about constant when a distance between the first and second grip members is less than 40 mm and from 2.50-2.75 N when the distance between the first and second grip members is 14 mm.

The vial engagement force may be about constant when a distance between the first and second grip members is less than 40 mm and from 3.00-3.25 N when the distance between the first and second grip members is 55 mm.

The vial engagement force may be both about constant when a distance between the first and second grip members is less than 40 mm and from 2.50-3.25 N when the distance between the first and second grip members is 5-55 mm.

The vial grip assembly may further include a center link, a first connecting link secured to the center link, a second connecting link secured to the center link, and a biasing member that biases the first grip member toward the second grip member with the vial engagement force, with the first grip member connected to the first connecting link, the second grip member connected to the second connecting link, and where movement of the first connecting link in a first direction results in movement of the second connecting link in a second direction opposite from the first direction. The center link may have a first end and a second end positioned opposite the second end, with the center link rotatable relative to the base about a central pivot, the first connecting link having a first end secured to the first end of the center link and a second end positioned opposite the first end of the first connecting link, and the second connecting link having a first end secured to the second end of the center link and a second end positioned opposite the first end of the second connecting link. The biasing member may be an extension spring having a first end secured to the center link and a second end secured to a post attached to the base. The vial grip assembly may further include a first grip link secured to the first connecting link and a second grip link secured to the second connecting link, with the base defining a first guide channel and a second guide channel, and where the first grip member is secured to the first grip link via a fastener extending through the first guide channel, and the second grip member is secured to the second grip link via a fastener extending through the second guide channel.

The first and second grip members may each include a cam surface and vial receiving surface, with the cam surfaces of the first and second grip members configured to engage a vial and move the first and second grip members away from each other, and the vial receiving surfaces of the first and second grip members configured to engage a vial. The cam surfaces may each be angled and together form a V-shape when the first and second grip members are positioned adjacent to each other. The vial receiving surface of the first and second grip members may each form a V-shaped recess.

The handle may be rotatable relative to the support member via a handle support, with the handle biased to the first position via a spring.

The device may further include first and second guide members extending from the base and an adapter grip base movable along the first and second guide members, with the vial adapter grip assembly secured to the adapter grip base and the handle received by and movable relative to the adapter grip base, where the adapter grip base is configured to move along the first and second guide members when the handle is moved from the first to the second position.

The vial adapter grip assembly may further include a press member having an engagement surface configured to engage a vial adapter. The adapter grip member may include an adapter main body and first and second adapter arms extending from the main body, with the first and second adapter arms each configured to move relative to the main body. The first and second adapter arms may define a semi-spherical surface. The adapter grip member may define an elongated slot positioned between the first and second adapter arms. The first and second adapter arms may each include a cam surface, and the cam surface may be configured to engage a vial adapter and bias the first and second adapter arms radially outward to engage and hold a vial adapter. The first and second adapter arms may each include a lip portion extending from the first and second adapter arms.

DETAILED DESCRIPTION

Figure 1:
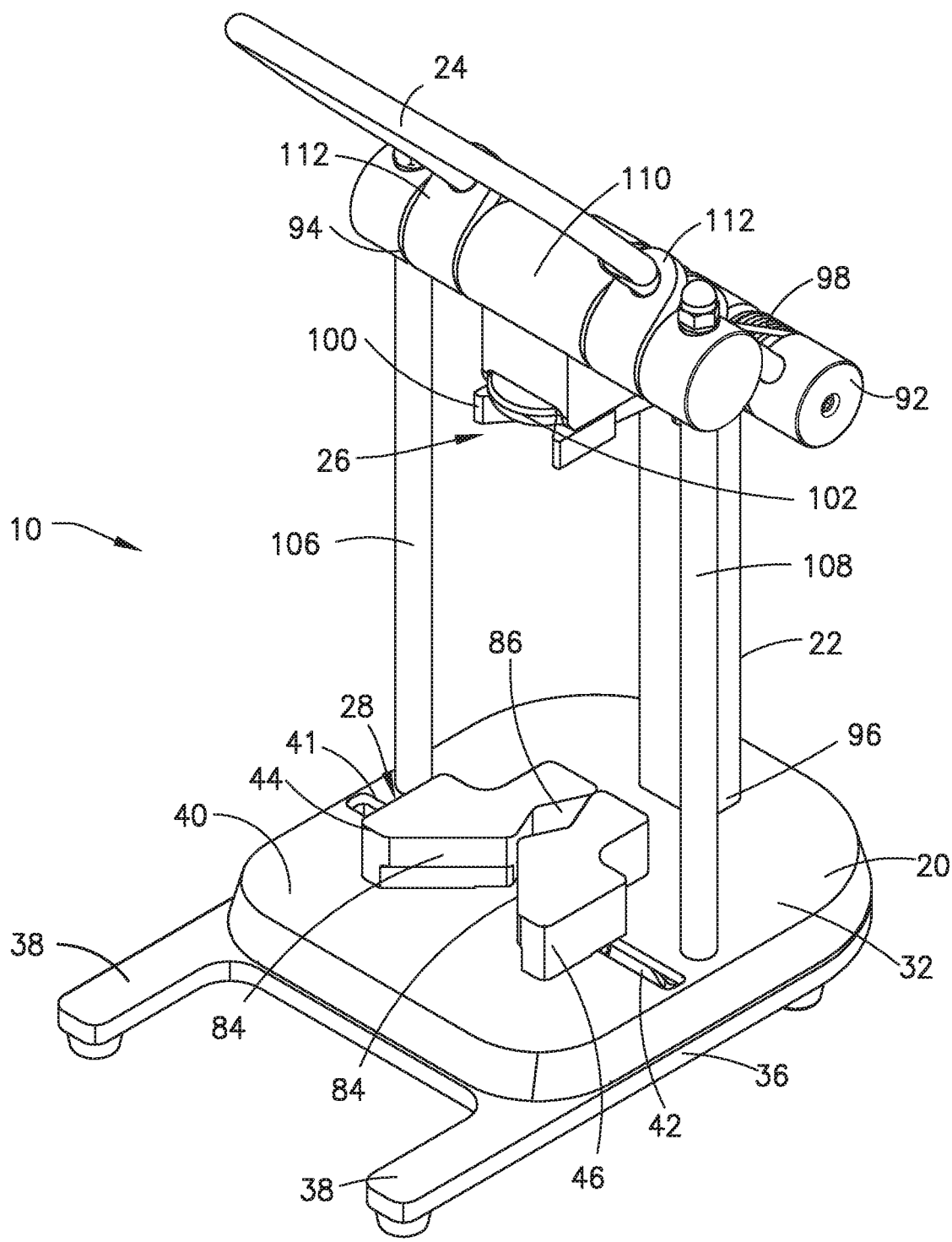
FIG. 1 is a perspective view of an assembly fixture device according to one aspect of the present invention.
Figure 2:
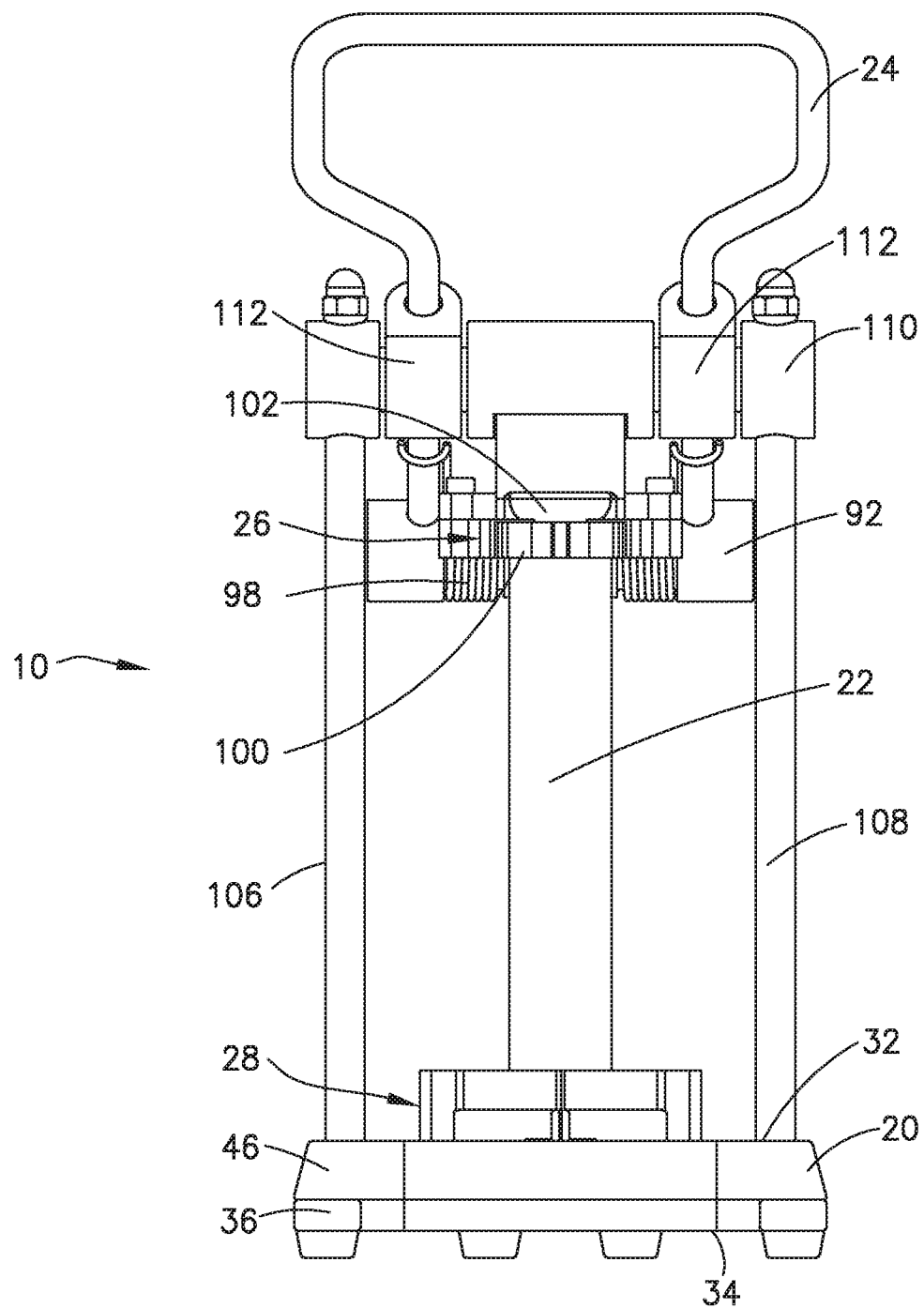
FIG. 2 is a front view of the device of FIG. 1.
Figure 3:
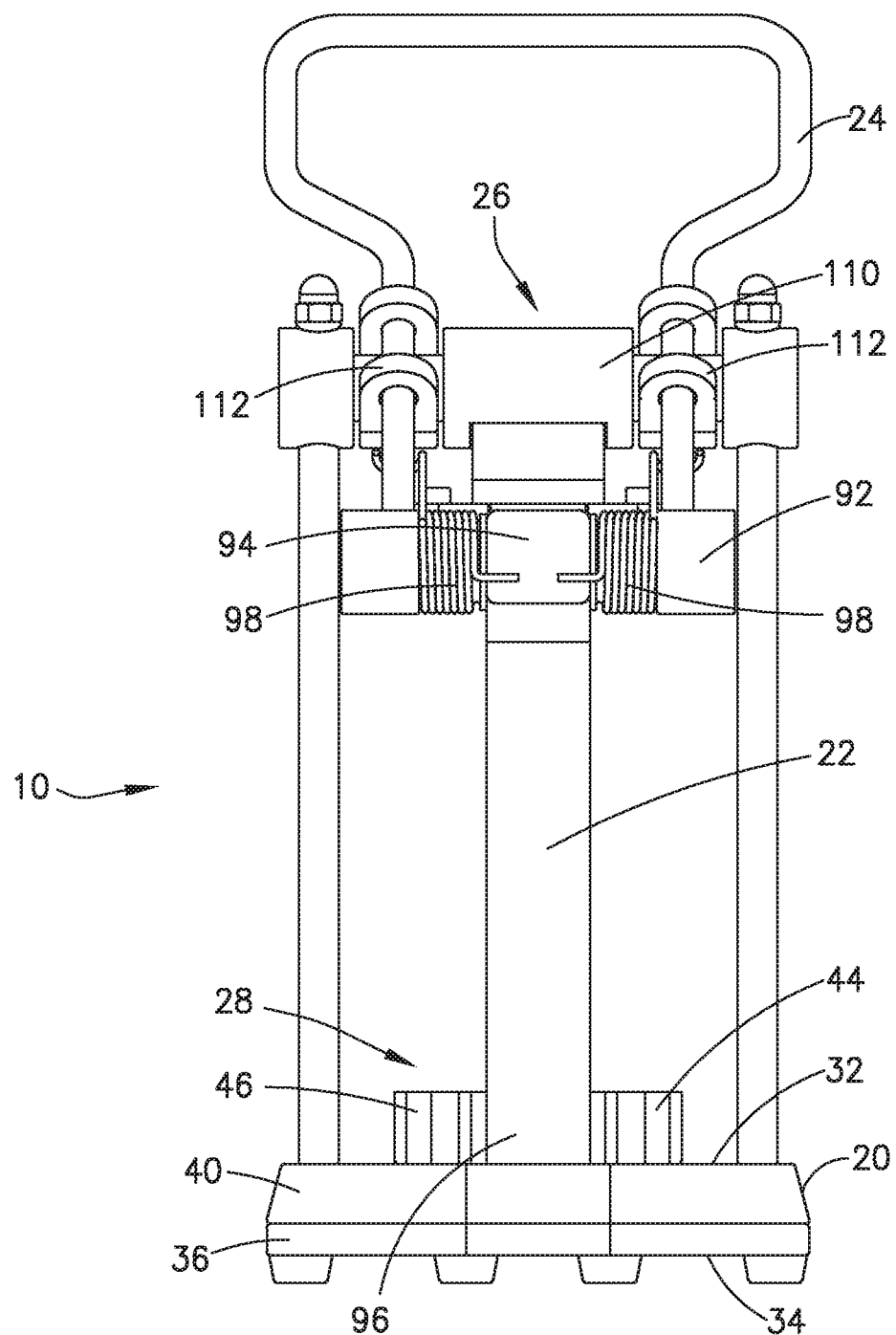
FIG. 3 is a rear view of the device of FIG. 1.
Figure 4:
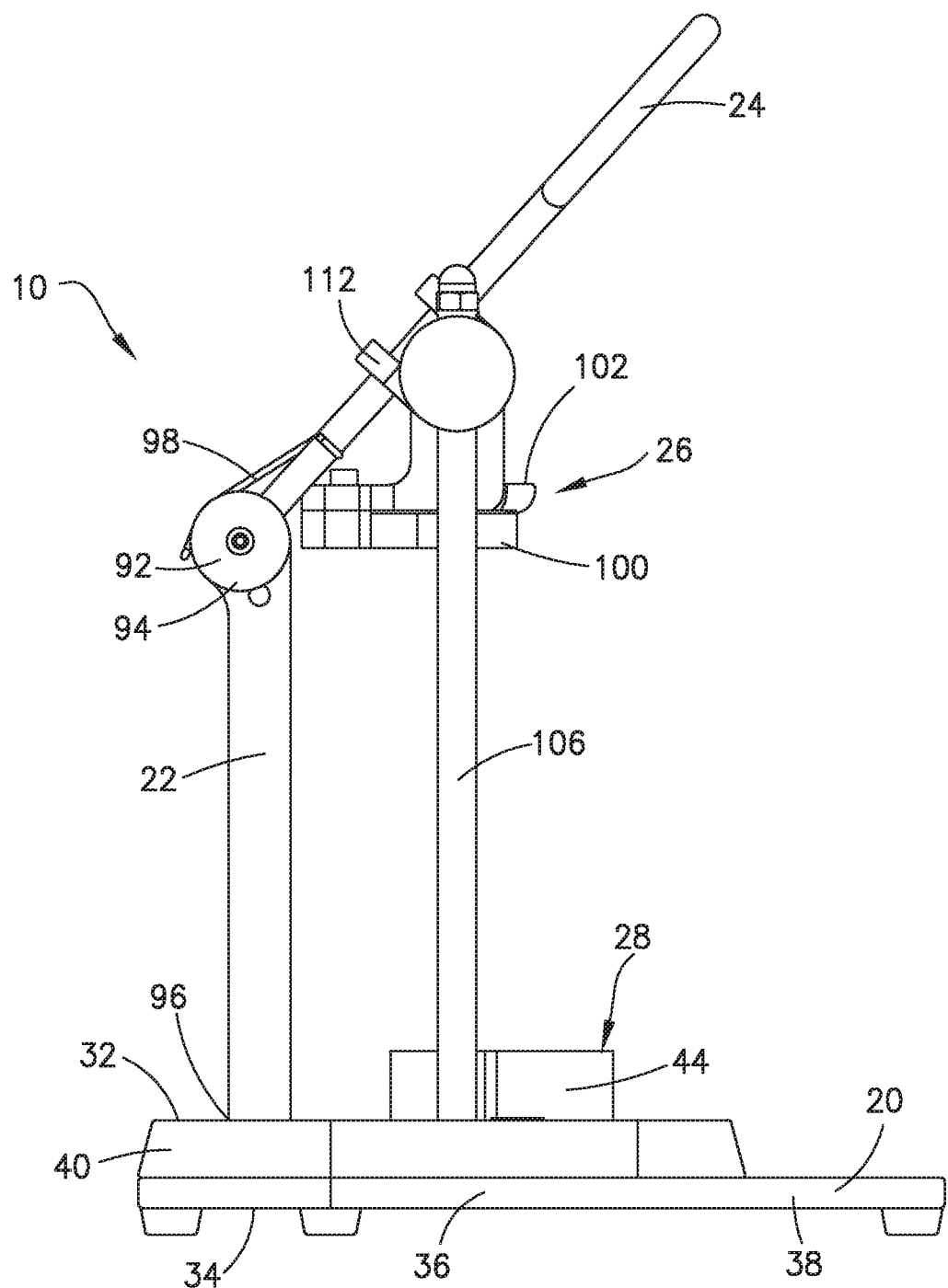
FIG. 4 is a side view of the device of FIG. 1.
Figure 5:
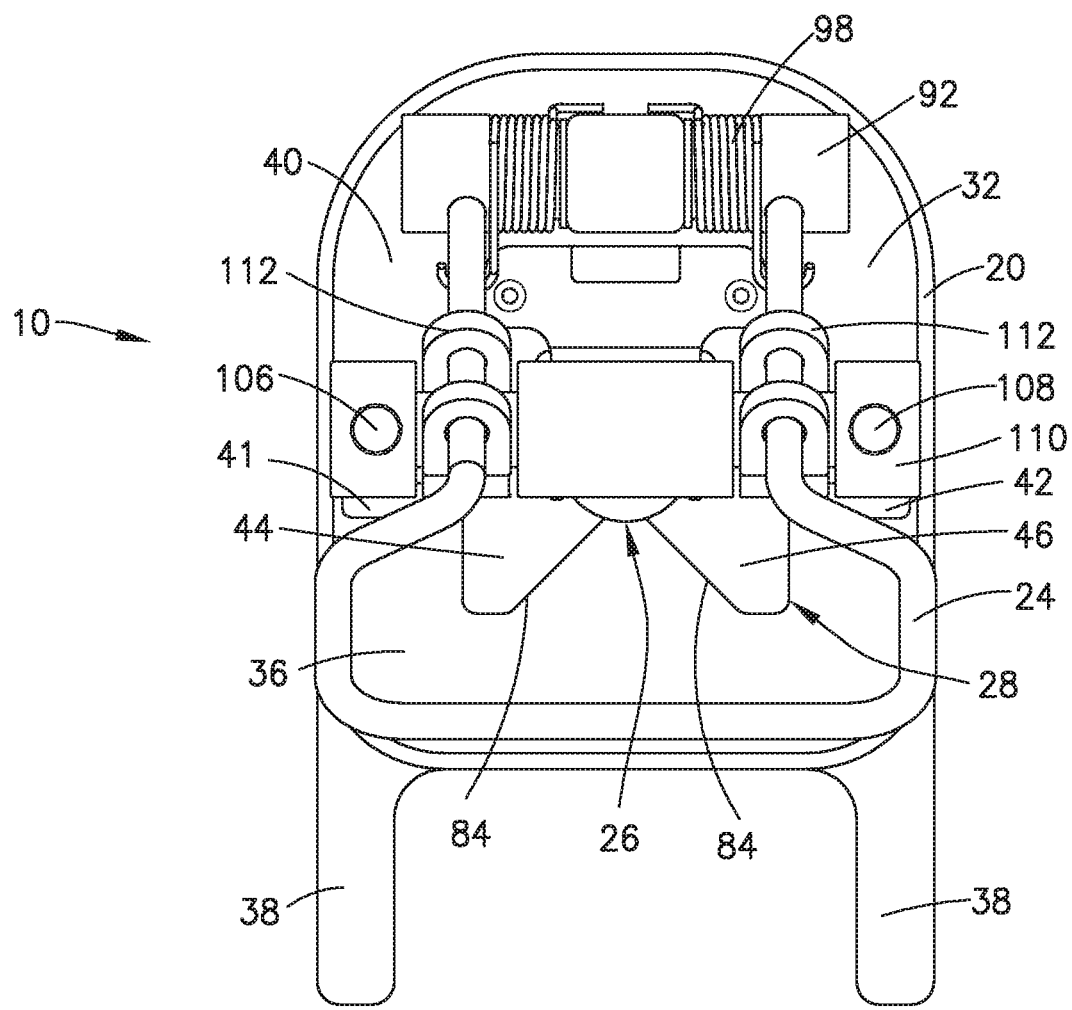
FIG. 5 is a top view of the device of FIG. 1.
Figure 6:
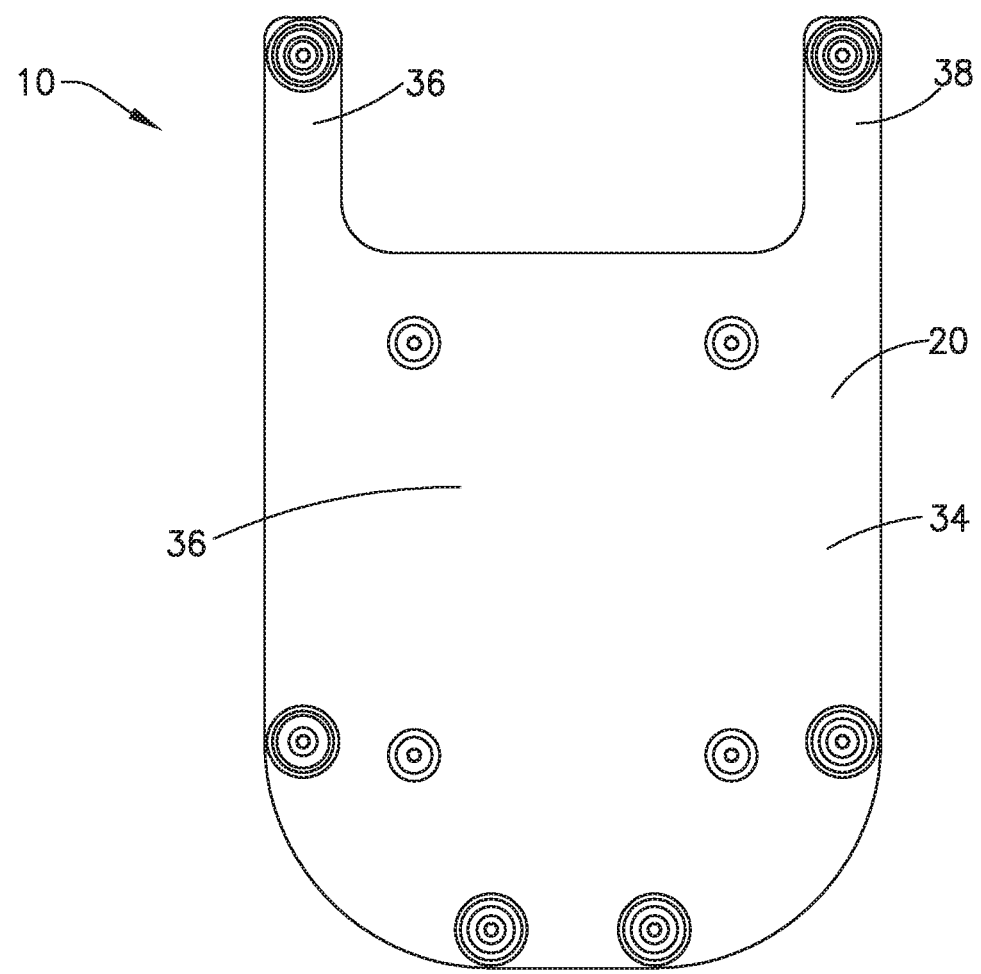
FIG. 6 is a bottom view of the device of FIG. 1.
Figure 7:
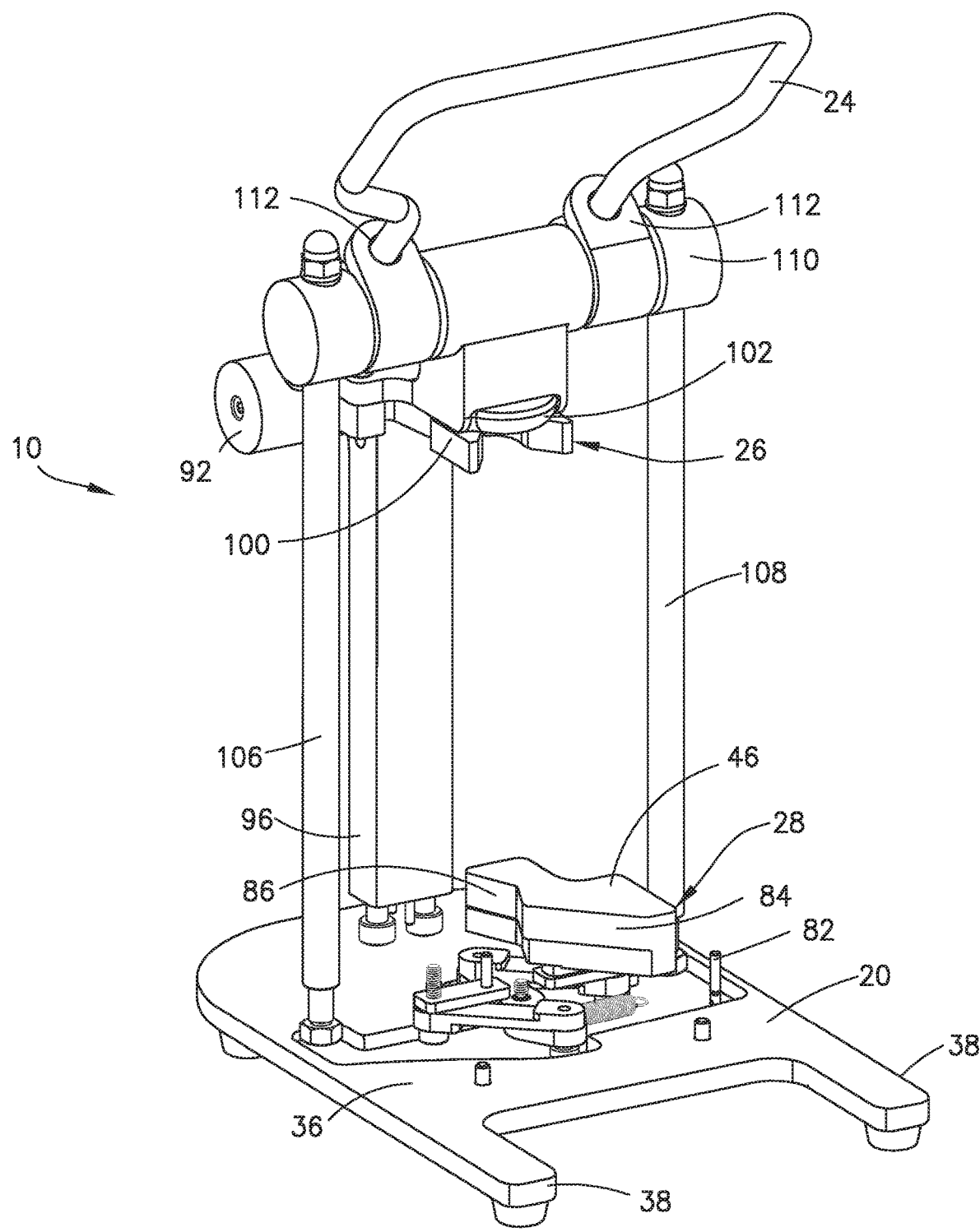
FIG. 7 is a perspective view of the device of FIG. 1, showing a cover plate removed for clarity.
Figure 8:
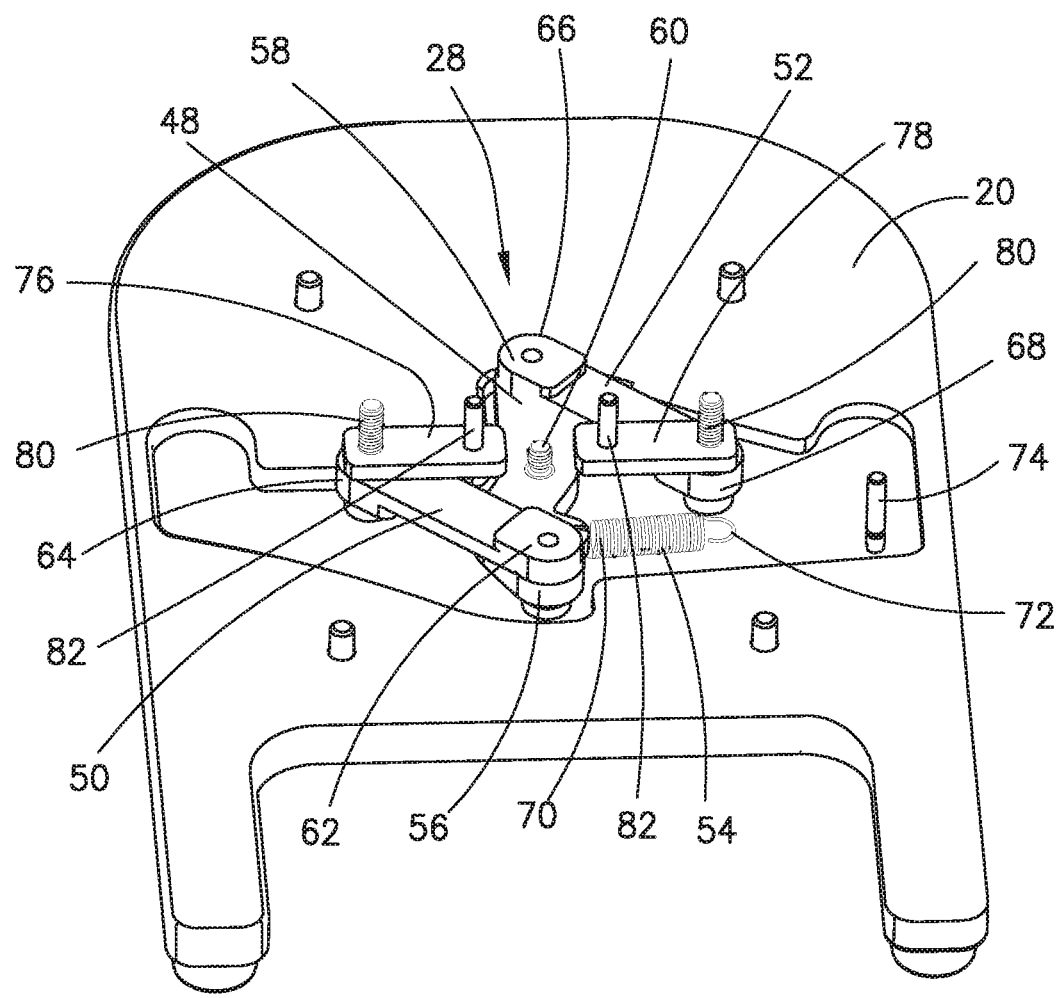
FIG. 8 is a perspective view of the device of FIG. 1, showing a vial grip assembly.
Figure 9:
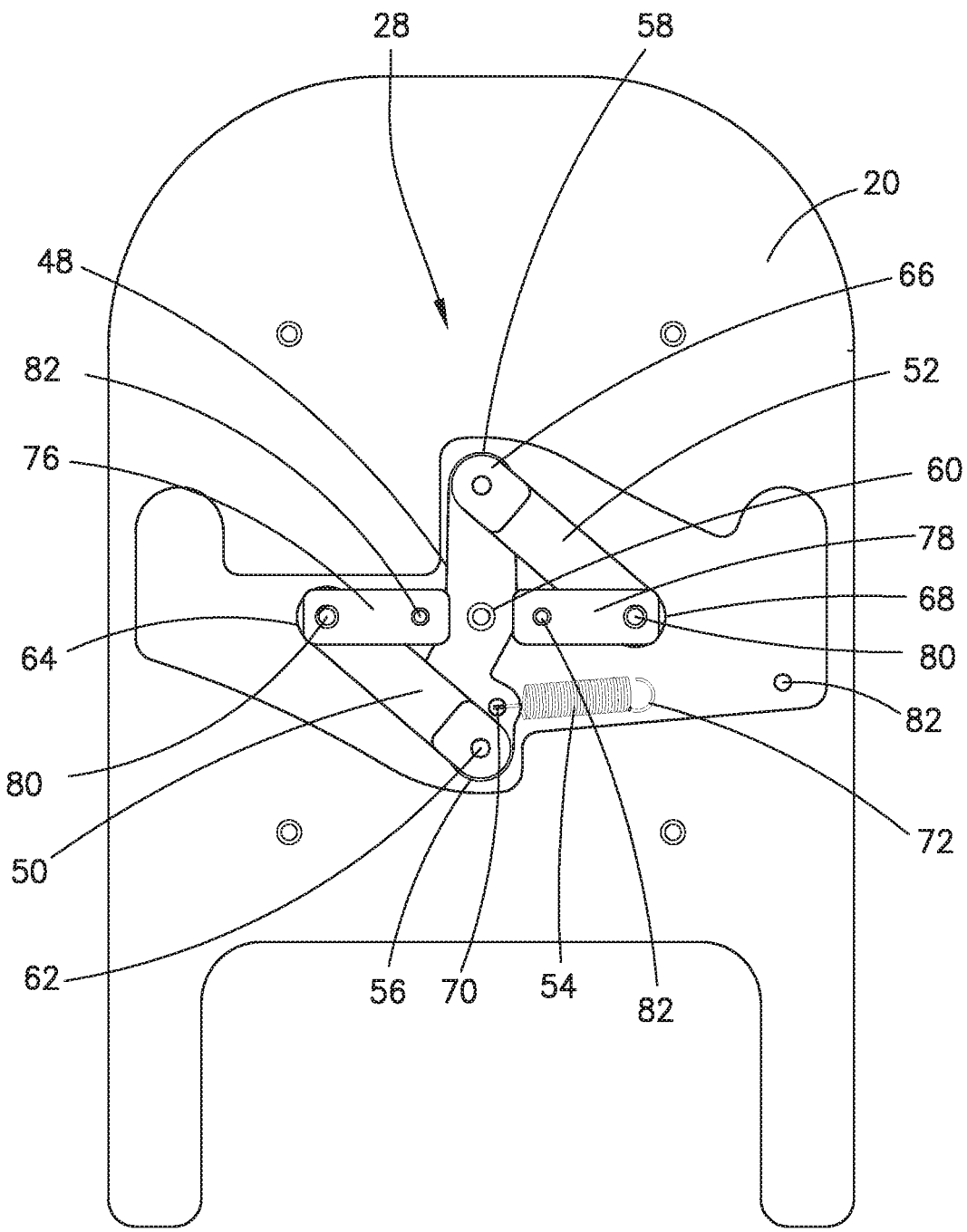
FIG. 9 is top view of the device of FIG. 1, showing a vial grip assembly.

For purposes of the description hereinafter, the terms such as "end", "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume various alternative variations and step sequences, except where expressly specified to the contrary. It is also to be understood that the specific devices and processes illustrated in the attached drawings, and described in the following specification, are simply exemplary embodiments of the invention. Hence, specific dimensions and other physical characteristics related to the embodiments disclosed herein are not to be considered as limiting. Further, it is to be understood that the invention may assume various alternative variations and step sequences, except where expressly specified to the contrary.

Referring to FIGS. 1-20, an assembly fixture device 10 for attaching a vial adapter to a vial, according to one aspect of the present invention, includes a base 20, a support member 22 secured to the base 20, a handle 24 connected to the support member 22, a vial adapter grip assembly 26 connected to the handle 24, and a vial grip assembly 28 connected to the base 20. The assembly fixture device 10 is configured to secure a vial adapter to a vial. In particular, the vial adapter grip assembly 26 is configured to engage and hold a vial adapter and the vial grip assembly 28 is configured to engage and hold a vial with the handle 24 being movable to press a vial adapter held by the vial adapter grip assembly 26 onto a vial held by the vial grip assembly 28.

Referring to FIGS. 1-9, the base 20 has a first side 32 and a second side 34 positioned opposite the first side 32. The base 20 includes a main body 36 having a pair of legs 38 extending from the main body 36. The base 20 also includes a cover 40 positioned on the main body 36. The cover 40 of the base 20 defines first and second guide channels 41,42, which are discussed in more detail below.

Referring to FIGS. 1-11, the vial grip assembly 28 includes first and second grip members 44,46 that are movable relative to each other and configured to engage and hold a vial. The first grip member 44 is biased toward the second grip member 46 to provide a vial engagement force, which secures a vial between the first and second grip members 44,46 during use of the device 10. The vial engagement force is ideally about constant regardless of the size of the vial positioned between the vial grip members 44,46 to ensure the vial remains stable during use of the device 10 while preventing excess forces from crushing or deforming the vial. The vial grip assembly 28 also includes a center link 48, a first connecting link 50 secured to the center link 48, a second connecting link 52 secured to the center link 48, and a biasing member 54 that biases the first grip member 44 toward the second grip member 46 to provide the vial engagement force. The first grip member 44 is connected to the first connecting link 50, the second grip member 46 is connected to the second connecting link 52, and movement of the first connecting link 50 in a first direction results in movement of the second connecting link 52 in a second direction opposite from the first direction. The center link 48 has a first end 56 and a second end 58 positioned opposite the first end 56. The center link 48 is rotatable relative to the base 20 about a central pivot 60, with the first connecting link 50 having a first end 62 secured to the first end 56 of the center link 48 and a second end 64 positioned opposite the first end 62 of the first connecting link 50, and the second connecting link 52 having a first end 66 secured to the second end 58 of the center link 48 and a second end 68 positioned opposite the first end 66 of the second connecting link 52. Then central pivot 60 is positioned between the first end 56 of the center link 48 and the second end 58 of the center link 48. The biasing member 54 is an extension spring having a first end 70 secured to the center link 48 and a second end 72 secured to a post 74 attached to the base 20, although other suitable biasing arrangements and configurations may be utilized.

The vial grip assembly 28 further includes a first grip link 76 secured to the first connecting link 50 and a second grip 78 link secured to the second connecting link 52. The first grip member 44 is secured to the first grip link 76 via a fastener 80 extending through the first guide channel 41, and the second grip member 46 is secured to the second grip link 78 via a fastener 80 extending through the second guide channel 42. As shown more clearly in FIG. 8, the first and second grip members 44,46 are secured to respective first and second grip links 76,78 via a screw 80 passing through the respective first and second connecting links 50,52, the respective first and second grip links 76,78 and into the respective first and second grip members 44,46. The first and second grip links 76,78 also each include a post 82 extending from the respective first and second grip links 76,78 and received by the respective first and second grip members 44,46. The first and second connecting links 50,52 are each rotatable relative to the center link 48.

Figure 10:
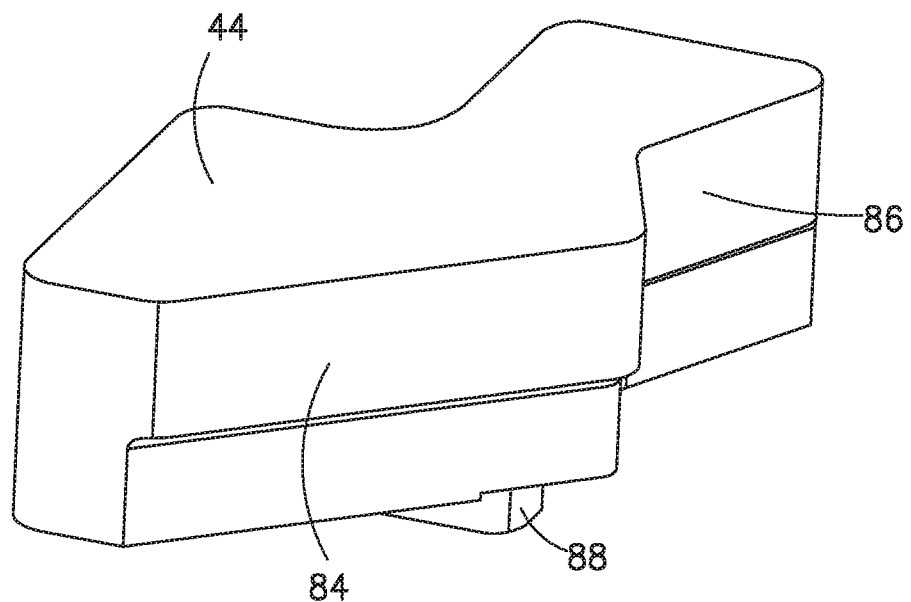
FIG. 10 is a top perspective view of a vial grip member according to one aspect of the present invention.
Figure 11:
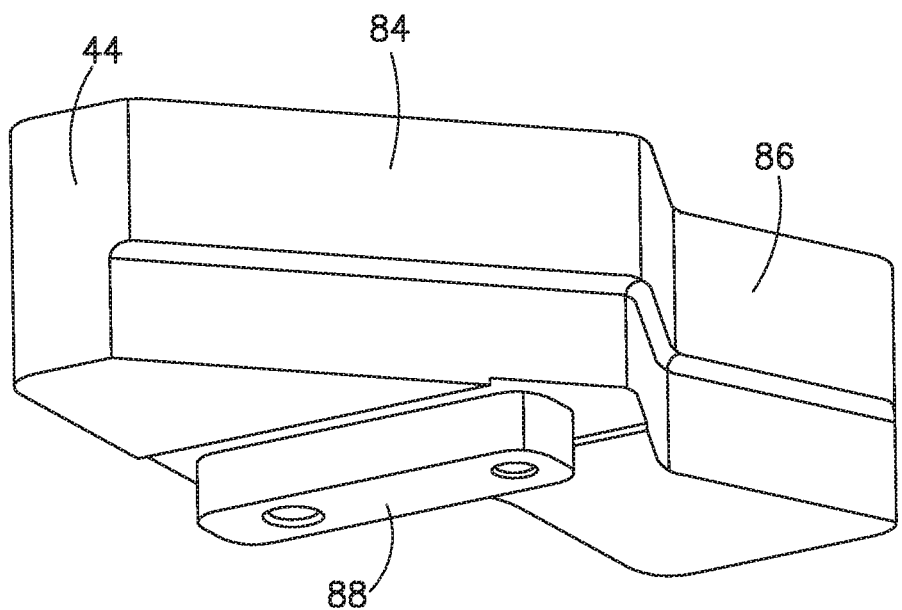
FIG. 11 is a bottom perspective view of the vial grip member of FIG. 10.
Figure 12:
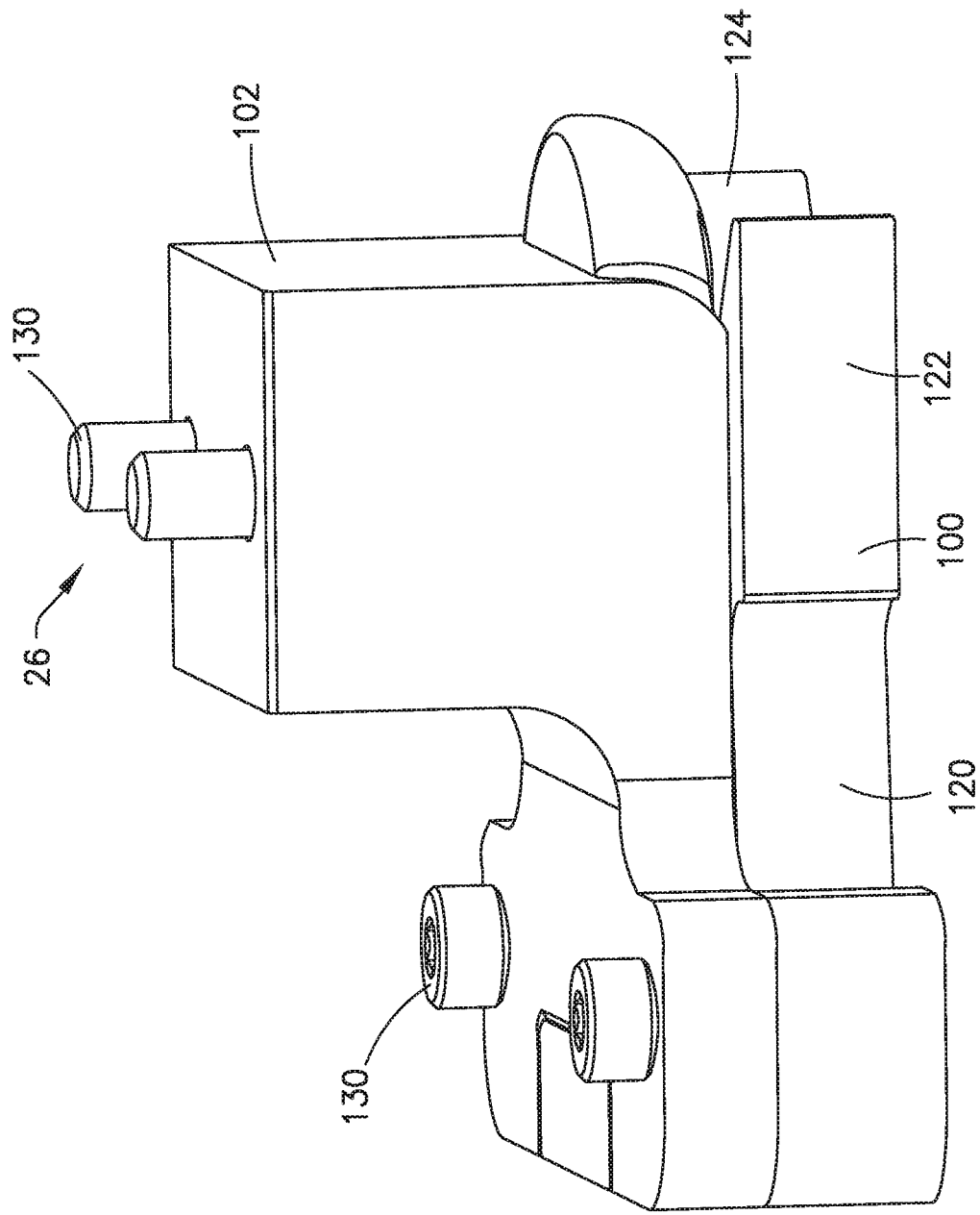
FIG. 12 is perspective view of a vial adapter grip assembly according to one aspect of the present invention.
Figure 13:
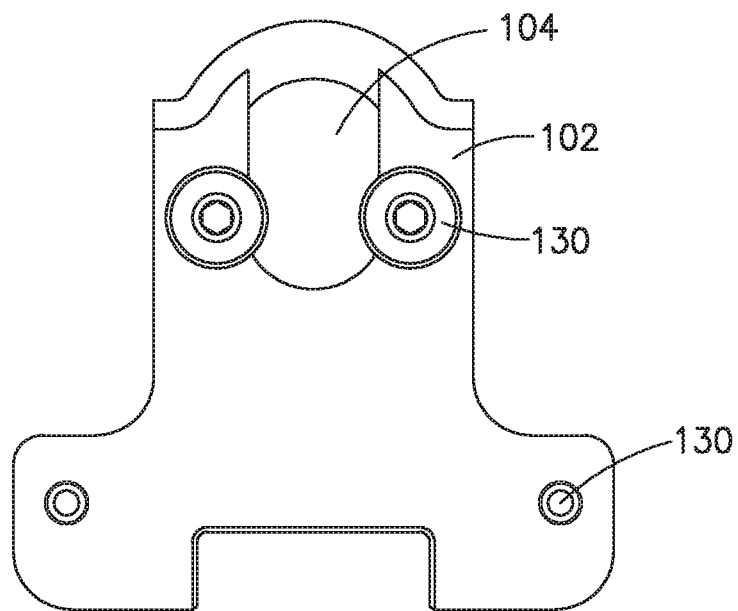
FIG. 13 is a bottom view of the vial adapter grip assembly of FIG. 12.
Figure 14:
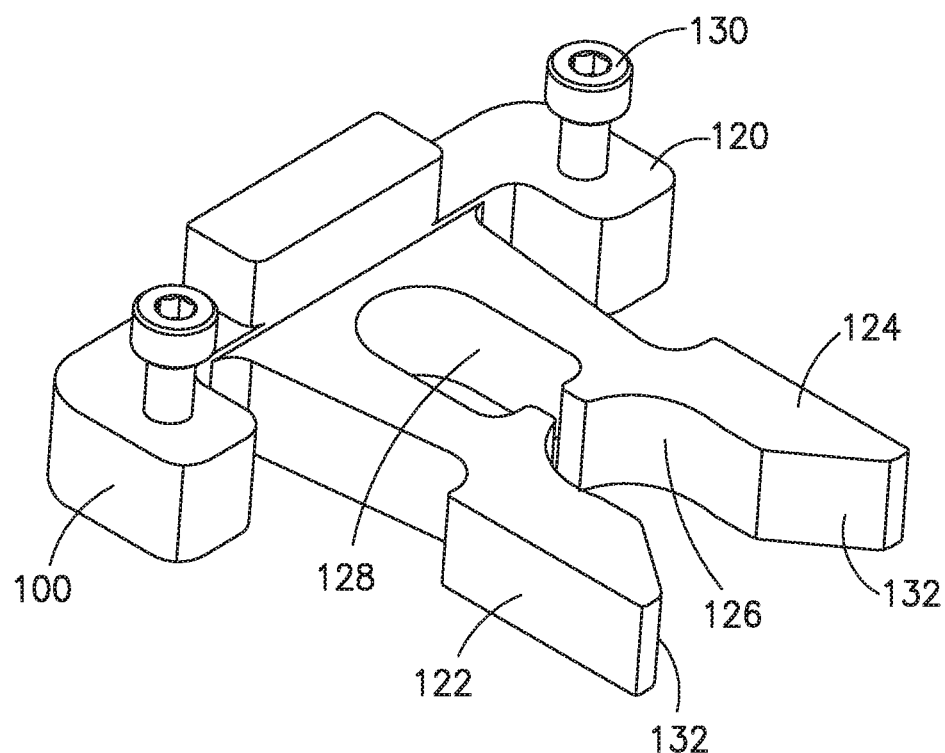
FIG. 14 is a perspective view of an adapter grip member according to one aspect of the present invention.
Figure 15:
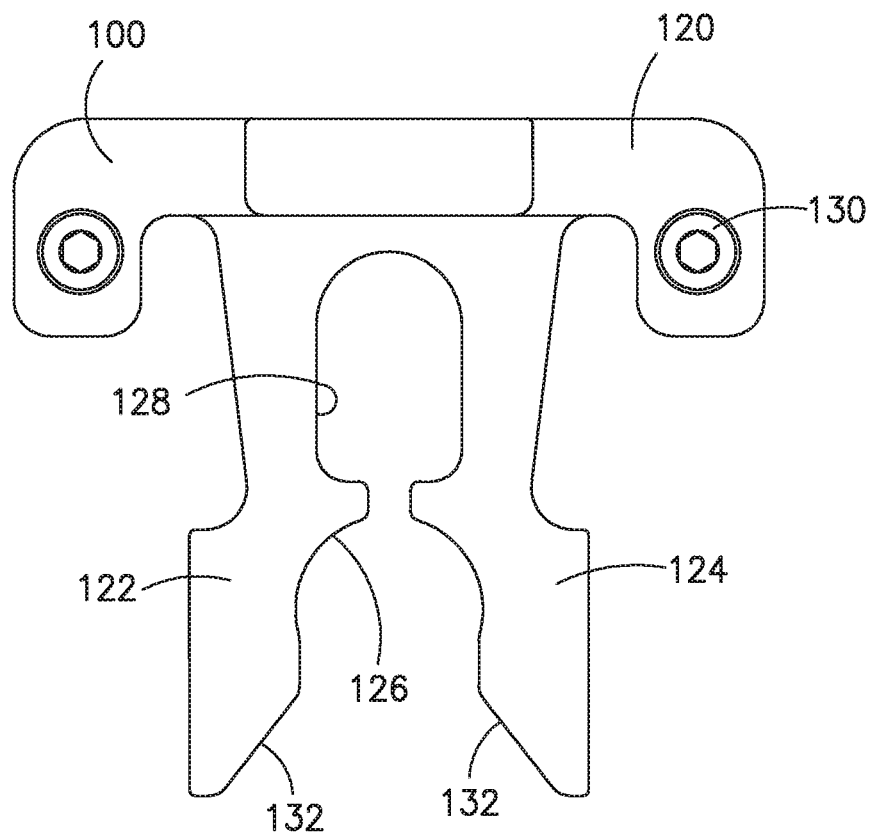
FIG. 15 is a top view of the adapter grip member of FIG. 14.
Figure 16:
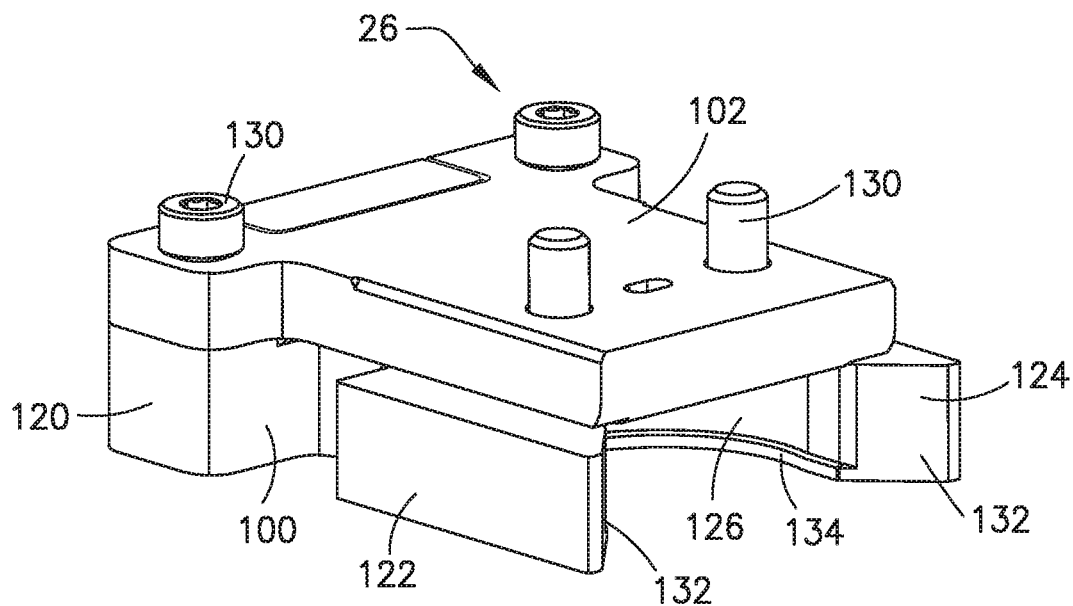
FIG. 16 is a top perspective view a vial adapter grip assembly according to a further aspect of the present invention.
Figure 17:
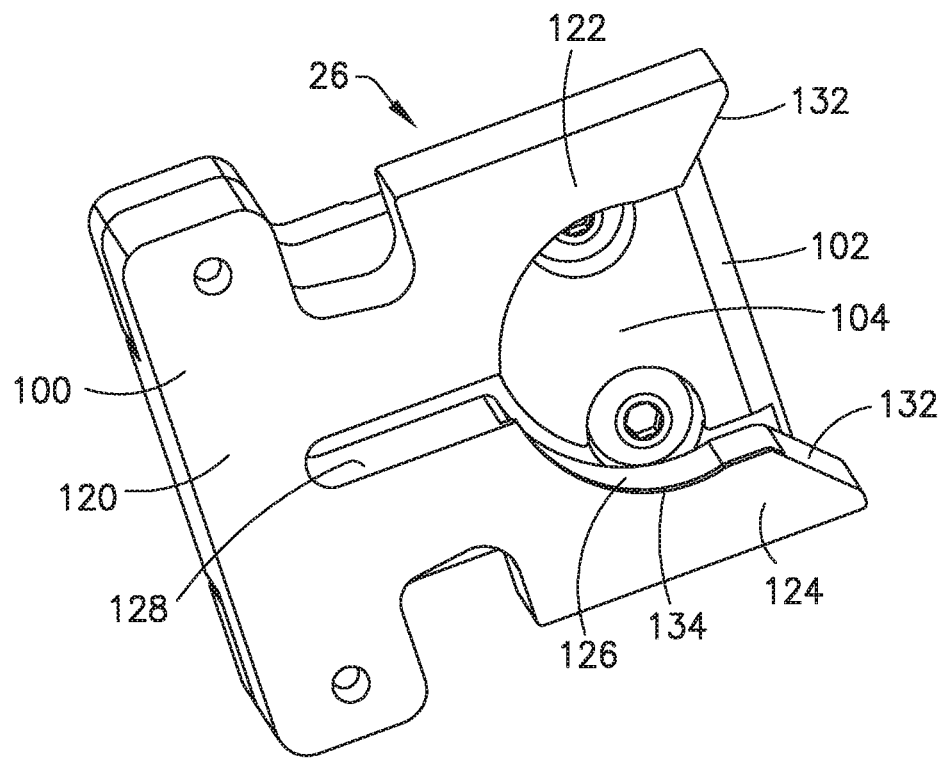
FIG. 17 is a bottom perspective view of the vial adapter grip assembly of FIG. 16.
Figure 18:
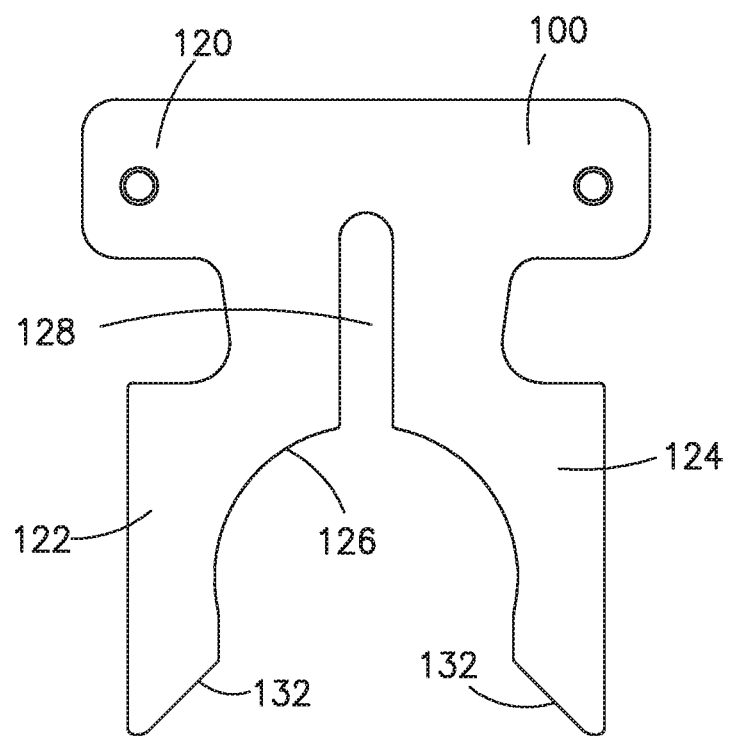
FIG. 18 is a bottom view of an adapter grip member according to a further aspect of the present invention.

Referring to FIGS. 10 and 11, the first and second grip members 44,46 each include a cam surface 84 and vial receiving surface 86, with the cam surfaces 84 of the first and second grip members 44,46 configured to engage a vial and move the first and second grip members 44,46 away from each other. The vial receiving surfaces 86 of the first and second grip members 44,46 are configured to engage a vial and to securely hold a vial between the first and second grip members 44,46. The cam surfaces 84 are each angled and together form a V-shape when the first and second grip members 44,46 are positioned adjacent to each other. Due the shape and angle of inclination of the cam surfaces 84, a vial pushed into the cam surfaces 84 of the first and second grip members 44,46 will produce a force acting transversely to the force from the vial thereby causing the first and second grip members 44,46 to open and move away from each other. The center link 48 will pivot ensuring the first and second grip members 44,46 move together at the same distance via the connection of each grip member 44,46 to the center link 48 through the grip links 76,78 and the connecting links 50,52. The vial is pushed forward until the first and second grip members 44,46 open sufficiently to receive the vial between the vial receiving surfaces 86 of the first and second grip members 44,46, with the vial engagement force securing the vial while the device 10 is operated. The vial receiving surface 86 of the first and second grip members 44,46 each may be formed as a V-shaped recess, although other suitable shapes and configurations may be utilized. The first and second grip members 44,46 also each include a guide projection 88 extending from the first and second grip members 44,46. The guide projections 88 of the first and second grip members 44,46 are received by and translate within the respective first and second guide channels 41,42 of the base 20.

Referring to FIGS. 1-5, the handle 24 is moveable between a first position and a second position. In particular, the handle 24 is rotatable relative to the support member 22 via a handle support 92 secured to a first end 94 of the support member 22 with a second end 96 of the support member 22 secured to the base 20. The handle 24 is biased to the first position via a spring 98. The spring 98 may be a torsion spring, although other suitable springs may be utilized. In one aspect, the handle 24 is cylindrical and formed generally into a U-shape, although other suitable shapes and configurations may be utilized.

Referring to FIGS. 1-5 and 12-19, the vial adapter grip assembly 26 includes an adapter grip member 100 configured to engage and hold a vial adapter and a press member 102 having an engagement surface 104 configured to engage a vial adapter. The vial adapter grip assembly 26 has a first position when the handle 24 is in the first position and a second position when the handle 24 is in the second position. The first position of the vile adapter grip assembly 26 may correspond to an initial position prior to assembly of a vial adapter onto a vial and the second position of the vile adapter grip assembly 26 may correspond to a final position after assembly of a vial adapter onto a vial. The device 10 further includes first and second guide members 106,108 extending from the base 20 and an adapter grip base 110 movable along the first and second guide members 106,108. The first and second guide members 106,108 are cylindrical, although other suitable shapes and configurations may be utilized. The vial adapter grip assembly 26 is secured to the adapter grip base 110. The handle 24 is received by and movable relative to the adapter grip base 110, with the adapter grip base 110 configured to move along the first and second guide members 106,108 when the handle 24 is moved from the first to the second position. More specifically, the handle 24 is received by a pair of lugs 112 of the adapter grip base 110 with a portion of the handle 24 sliding through the lugs 112 as the handle 24 moves from the first position to the second position. Downward movement of the handle 24 forces the adapter grip base 110 and vial adapter grip assembly 26 to move downward along the guide members 106,108 with the handle 24 sliding through the lugs 112 as the handle 24 continues to move downward. Moving the handle 24 upward or allowing the spring 98 to bias the handle 24 upward reverses the process to move the adapter grip base 110 upward via engagement between the handle 24 and the lugs 112 of the adapter grip base 110. The adapter grip base 110 and the guide members 106,108 allow the vial adapter grip assembly 26 to move linearly between the first and second positions while the handle 24 pivots about an axis defined by the handle support 92. The sliding movement between the handle 24 and the adapter grip base 110 allows the rotational movement of the handle 24 to be translated to the linear movement of the adapter grip base 110, although other suitable arrangements and configurations may be utilized.

Referring to FIGS. 12-19, one or more configurations for the adapter grip member 100 and press member 102 may be provided to accommodate various type of vial adapters. The adapter grip member 100 and press member 102 shown in FIGS. 12-15, for example, are configured to engage and hold a PhaSeal™ vial adapter, which is commercially available from Becton, Dickinson and Company. The adapter grip member 100 and press member 102 shown in FIGS. 16-19 are configured to engage and hold an alternative vial adapter design. The adapter grip members 100 and press members 102, however, include similar features, which are discussed in more detail below.

Figure 19:
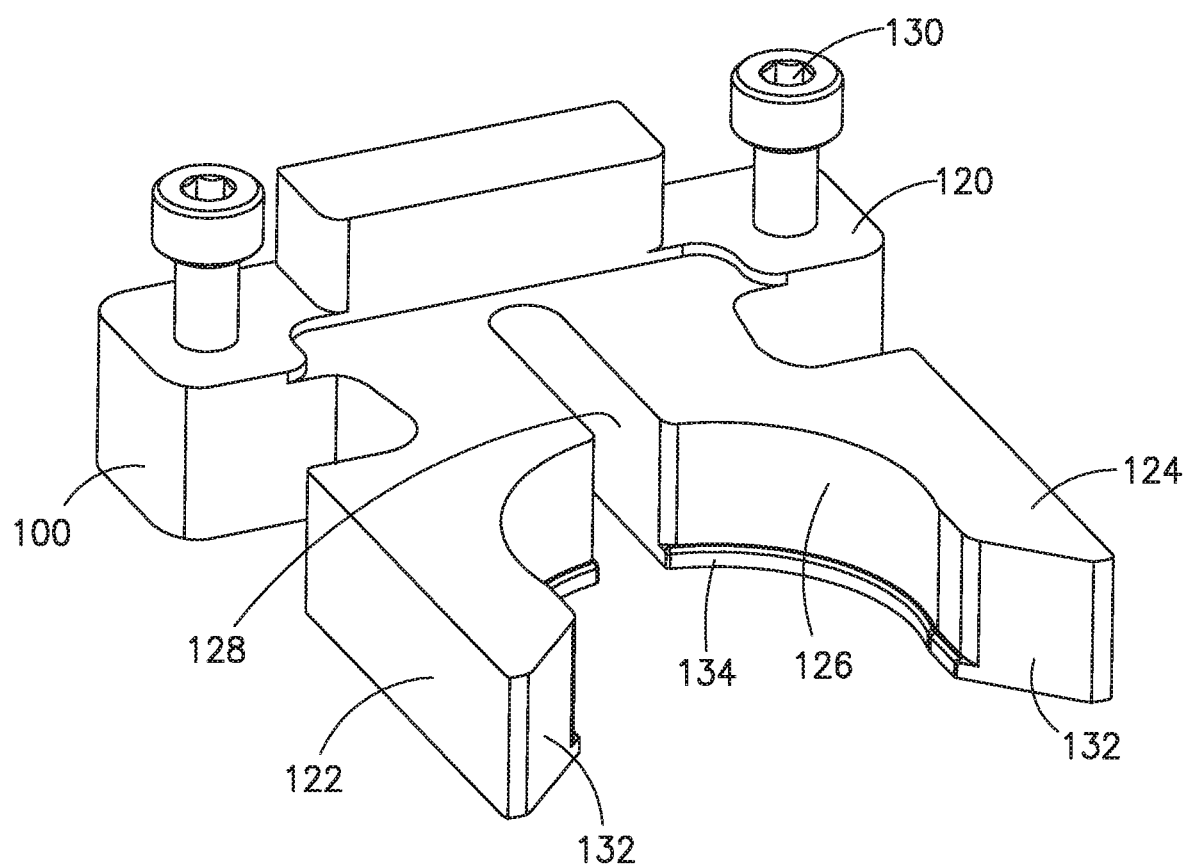
FIG. 19 is a perspective view of the adapter grip member of FIG. 18.

The adapter grip member 100 includes an adapter main body 120 and first and second adapter arms 122,124 extending from the main body 120, with the first and second adapter arms 122,124 each configured to move relative to the main body 120. More specifically, due to their shape, the first and second adapter arms 122,124 are configured to deflect radially outward when engaged by a vial adapter. The first and second adapter arms 122,124 may be made from a thermoplastic material, such as a polymer, an elastomeric material, or any other suitable material. The first and second adapter arms 122,124 define a semi-spherical engagement surface 126, although other suitable shapes and configurations may be utilized. The adapter grip member 100 defines an elongated slot 128 positioned between the first and second adapter arms 122,124, which facilities the deflection of the first and second adapter arms 122,124. The press member 102 is secured to the adapter grip member 100 via one or more fasteners 130 with the press member 102 being secured to the adapter grip base 110 via one or more fasteners 130. The engagement surface 104 of the press member 102 is aligned with and positioned above the first and second adapter arms 122,124 such that the engagement surface 104 is positioned above a vial adapter when a vial adapter abuts the semi-spherical engagement surface 126 of the adapter main body 120. The first and second adapter arms 122,124 each include a cam surface 132, with the cam surface 132 configured to engage a vial adapter and bias the first and second adapter arms 122,124 radially outward to engage and hold a vial adapter. More specifically, engagement of the cam surfaces 132 of the first and second adapter arms 122,124 with a vial adapter forces the first and second adapter arms 122,124 radially outward with a portion of the vial adapter abutting the semi-spherical engagement surface 126. The first and second adapter arms 122,124 engage and hold the vial adapter in position for securing the vial adapter to the vial. As shown in FIG. 19, the first and second adapter arms 122,124 may each include a lip portion 134 extending from the first and second adapter arms 122,124.

Figure 20:
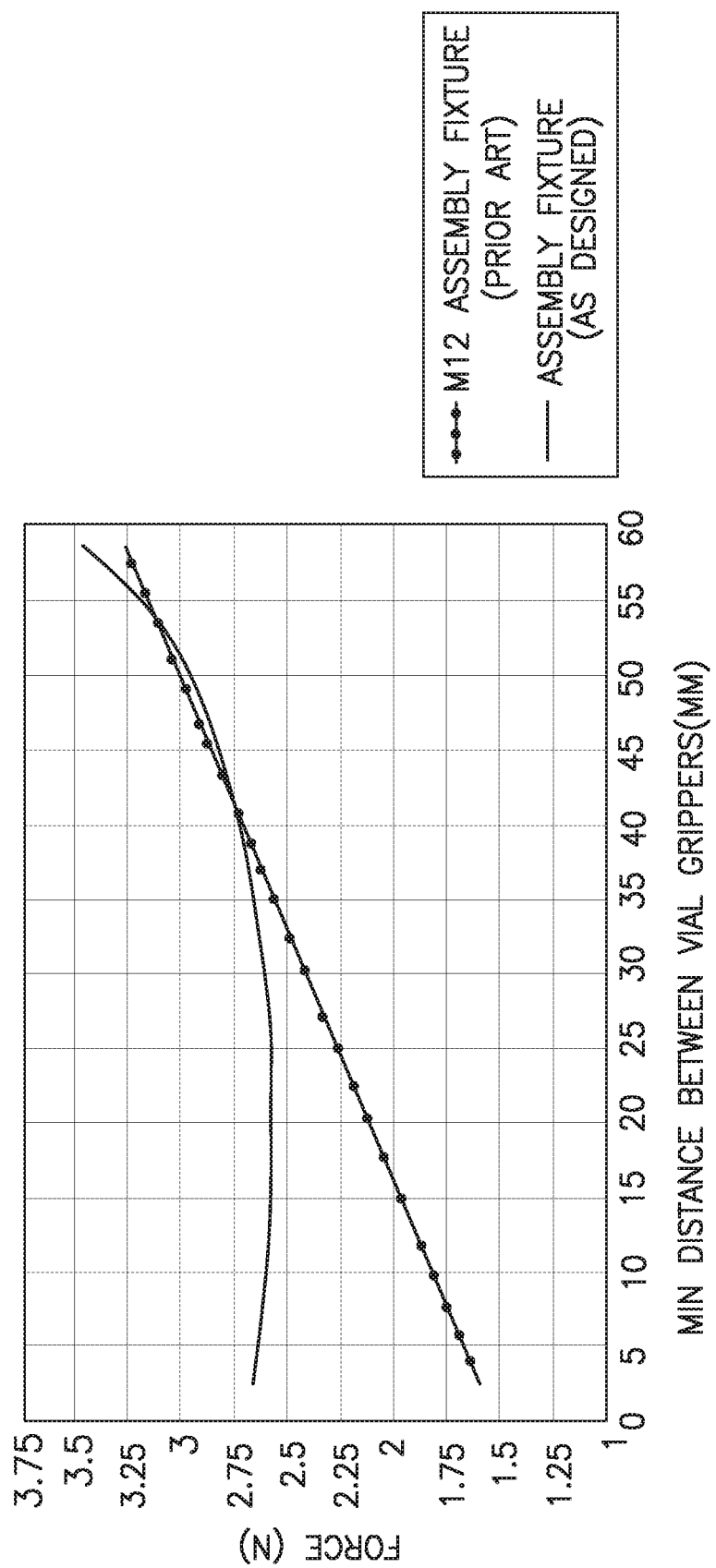
FIG. 20 is a chart illustrating a vial engagement force (y-axis) versus a distance between first and second grip members (x-axis) for a conventional assembly fixture device and the assembly fixture device of FIG. 1.

Referring to FIG. 20, the vial grip assembly 28 of the device 10 is configured to provide a constant vial engagement force regards of the size of vial utilized in connection with the device 10. FIG. 20 compares a force (N) versus distance between vial grip members (mm) for a convention assembly fixture and the assembly fixture device 10 of FIGS. 1-19. In one aspect, the vial engagement force is about constant when a distance between the first and second grip members 44,46 is less than 40 mm. In a further aspect, the vial engagement force is 2.50-2.75 N when the distance between the first and second grip members 44,46 is less than 40 mm. In another aspect, the vial engagement force is 2.50-2.75 N when the distance between the first and second grip members 44,46 is 14 mm and 3.00-3.25 N when the distance between the first and second grip members 44,46 is 55 mm. In yet another aspect, the vial engagement force is 2.50-3.25 N when the distance between the first and second grip members 44,46 is 5-55 mm. The distance between the first and second grip members 44,46 corresponds to various sized vials having various sizes of diameters.

While certain exemplary embodiments of the present invention have been shown and described herein with reference to certain preferred embodiments thereof, it will be understood by those skilled in the art that various changes in form and details may be made therein without departing from the spirit and scope of the invention.

The invention claimed is:

1. An assembly fixture device for attaching a vial adapter to a vial, the device comprising:
   a base having a first side and a second side positioned opposite the first side;
   a support member secured to the base, the support member having a first end and a second end positioned opposite the first end;
   a handle connected to the support member, the handle is movable between a first position and a second position;
   a vial adapter grip assembly connected to the handle, the vial adapter grip assembly comprising an adapter grip member configured to engage and hold the vial adapter, the vial adapter grip assembly having a first position when the handle is in the first position and a second position when the handle is in the second position; and
   a vial grip assembly connected to the base, the vial grip assembly comprising:
   first and second grip members that are movable relative to each other and configured to engage and hold the vial;
   a center link having a first end, a second end opposite the first end, and a central pivot positioned between the first end and the second end;
   a first connecting link connecting the first end of the center link to the first grip member;
   a second connecting link connecting the second end of the center link to the second grip member; and
   a biasing member that biases the first grip member toward the second grip member to provide a vial engagement force.

2. The device of claim 1, wherein the vial engagement force is about constant when a distance between the first and second grip members is less than 40 mm.

3. The device of claim 2, wherein the vial engagement force is from 2.50-2.75 N when the distance between the first and second grip members is less than 40 mm.

4. The device of claim 2, wherein the vial engagement force is from 2.50-2.75 N when the distance between the first and second grip members is 14 mm and from 3.00-3.25 N when the distance between the first and second grip members is 55 mm.

5. The device of claim 2, wherein the vial engagement force is from 2.50-3.25 N when the distance between the first and second grip members is 5-55 mm.

6. The device of claim 1, wherein the biasing member comprises an extension spring having a first end secured to the center link and a second end secured to the base.

7. The device of claim 1, wherein the vial grip assembly further comprises a first grip link secured to the first connecting link and a second grip link secured to the second connecting link, the base defining a first guide channel and a second guide channel, and wherein the first grip member is secured to the first grip link via a fastener extending through the first guide channel, and the second grip member is secured to the second grip link via a fastener extending through the second guide channel.

8. The device of claim 1, wherein the first and second grip members each comprise a cam surface and a vial receiving surface, the cam surfaces of the first and second grip members are configured to engage the vial and move the first and second grip members away from each other, and the vial receiving surfaces of the first and second grip members configured to engage the vial.

9. The device of claim 8, wherein the cam surfaces are each angled and together form a V-shape when the first and second grip members are positioned adjacent to each other.

10. The device of claim 8, wherein the vial receiving surface of the first and second grip members each comprise a V-shaped recess.

11. The device of claim 1, wherein the handle is rotatable relative to the support member via a handle support, the handle biased to the first position via a spring.

12. The device of claim 11, further comprising first and second guide members extending from the base and an adapter grip base movable along the first and second guide members, the vial adapter grip assembly secured to the adapter grip base, the handle received by and movable relative to the adapter grip base, wherein the adapter grip base is configured to move along the first and second guide members when the handle is moved from the first to the second position.

13. The device of claim 1, wherein the vial adapter grip assembly further comprises a press member having an engagement surface configured to engage the vial adapter.

14. The device of claim 13, wherein the adapter grip member comprises an adapter main body and first and second adapter arms extending from the main body, the first and second adapter arms are each configured to move relative to the main body.

15. The device of claim 14, wherein the first and second adapter arms define a semi-spherical surface.

16. The device of claim 14, wherein the adapter grip member defines an elongated slot positioned between the first and second adapter arms.

17. The device of claim 14, wherein the first and second adapter arms each include a cam surface, and wherein the cam surface is configured to engage the vial adapter and bias the first and second adapter arms radially outward to engage and hold the vial adapter.

18. The device of claim 14, wherein the first and second adapter arms each include a lip portion extending from the first and second adapter arms.

* * * * *